United States Patent
Govindjee et al.

(10) Patent No.: US 10,610,161 B1
(45) Date of Patent: Apr. 7, 2020

(54) DIAGNOSIS USING A DIGITAL ORAL DEVICE

(71) Applicant: International Business Machines Corporation, Armonk, NY (US)

(72) Inventors: Anita Govindjee, Ithaca, NY (US); Su Liu, Austin, TX (US); Cheng Xu, Beijing (CN); Hong Chuan Yuan, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/238,944

(22) Filed: Jan. 3, 2019

(51) Int. Cl.
*A61B 5/00* (2006.01)
*A61B 1/24* (2006.01)
(Continued)

(52) U.S. Cl.
CPC ........ *A61B 5/7264* (2013.01); *A46B 15/0016* (2013.01); *A46B 15/0055* (2013.01);
(Continued)

(58) Field of Classification Search
CPC .... G16H 10/60; G16H 30/20; A46B 15/0016; A46B 15/0055; A61B 1/00016;
(Continued)

(56) References Cited

U.S. PATENT DOCUMENTS

| | | | |
|---|---|---|---|
| 7,444,071 B2 | 10/2008 | Chen | |
| 2004/0151379 A1* | 8/2004 | Kim | A61B 5/416 382/209 |

(Continued)

FOREIGN PATENT DOCUMENTS

| | | |
|---|---|---|
| CN | 203970354 | 12/2014 |
| JP | 2009028058 | 2/2009 |

OTHER PUBLICATIONS

M.-C. Hu, "Automated tongue diagnosis on the smartphone and its applications." Comput Methods Programs Biomed. Dec. 24, 2017. pii: S0169-2607(17)30847-7. doi: 10.1016/j.cmpb.2017.12.029. [Epub ahead of print], Retrieved from Internet: https://www.ncbi.nlm.nih.gov/pubmed/29307471, 28 pages.
(Continued)

*Primary Examiner* — Edward Park
(74) *Attorney, Agent, or Firm* — Schmeiser, Olsen & Watts, LLP; Mark Vallone

(57) ABSTRACT

A system and method for instant tongue sampling and diagnosis includes acquiring a plurality of tongue images from a plurality of digital oral devices, and a current health conditions, building a diagnosis framework for diagnosing a current health condition of a user by: i) analyzing the collected tongue images with a visual recognition engine to determine tongue characteristics of each tongue captured in the tongue images, and ii) correlating the tongue characteristics with the current health condition, identifying tongue characteristics from a received image of the tongue using the visual image recognition engine, applying the diagnosis framework to the tongue characteristics of the tongue to diagnosis the current health condition of the user, and modifying a graphical user interface of the digital oral device to display a custom health report indicative of the current health condition of the user, in response to applying the diagnosis framework.

20 Claims, 9 Drawing Sheets

(51) Int. Cl.
*A61B 1/00* (2006.01)
*A61B 1/05* (2006.01)
*A46B 15/00* (2006.01)
*A61B 5/01* (2006.01)
*G16H 30/20* (2018.01)
*G16H 10/60* (2018.01)

(52) U.S. Cl.
CPC ...... *A61B 1/00016* (2013.01); *A61B 1/00039* (2013.01); *A61B 1/00045* (2013.01); *A61B 1/05* (2013.01); *A61B 1/24* (2013.01); *A61B 5/01* (2013.01); *G16H 10/60* (2018.01); *G16H 30/20* (2018.01); *A61B 5/0008* (2013.01)

(58) Field of Classification Search
CPC ... A61B 1/00039; A61B 1/00045; A61B 1/05; A61B 1/24; A61B 5/01
See application file for complete search history.

(56) References Cited

U.S. PATENT DOCUMENTS

| | | |
|---|---|---|
| 2008/0139966 A1 | 6/2008 | Zhang et al. |
| 2013/0061412 A1* | 3/2013 | Vashi ............... A46B 5/0095 15/106 |
| 2013/0122468 A1* | 5/2013 | Abrams ............... A61B 6/14 433/215 |

OTHER PUBLICATIONS

J. Ma, "Tongue image constitution recognition based on Complexity Perception method."(Submitted on Mar. 1, 2018) Retrieved from Internet: https://arxiv.org/abs/1803.00219, 12 pages.

M. Tania, "Computational complexity of image processing algorithms for an intelligent mobile enabled tongue diagnosis scheme," 2016 10th International Conference on Software, Knowledge, Information Management & Applications (SKIMA), Chengdu, 2016, pp. 29-36.

X. Wang, "Statistical Analysis of Tongue Images for Feature Extraction and Diagnostics," in IEEE Transactions on Image Processing, vol. 22, No. 12, pp. 5336-5347, Dec. 2013.

* cited by examiner

DIAGNOSIS USING A DIGITAL ORAL DEVICE

TECHNICAL FIELD

The present invention relates to systems and methods for instant tongue sampling and diagnosis, and more specifically the embodiments of a health diagnosis system for instant tongue sampling and diagnosis of a current user health condition.

BACKGROUND

Physical characteristics of a user's tongue can be indicative of a health condition of a person. The physical characteristics of the tongue can be manually observed by a practitioner, and based on the observation of the physical characteristics of the tongue, the practitioner can diagnose a health condition of the user.

SUMMARY

An embodiment of the present invention relates to a method, and associated computer system and computer program product, for instant tongue sampling and diagnosis of a current user health condition. A processor of a computing system acquires a plurality of tongue images from a plurality of digital oral devices associated with a plurality of users, and a current health condition of the plurality of users. A diagnosis framework for diagnosing a current health condition of a user is built by: i) analyzing the collected tongue images with a visual recognition engine to determine tongue characteristics of each tongue captured in the tongue images, and ii) correlating the tongue characteristics with the current health condition. An image of a tongue of the user is received from a digital oral device associated with the user. Tongue characteristics are identified from the image of the tongue using the visual image recognition engine. The diagnosis framework is applied to the tongue characteristics of the tongue to diagnosis the current health condition of the user. A graphical user interface of the digital oral device is modified to display a custom health report indicative of the current health condition of the user, in response to applying the diagnosis framework

DETAILED DESCRIPTION

Figure 1:
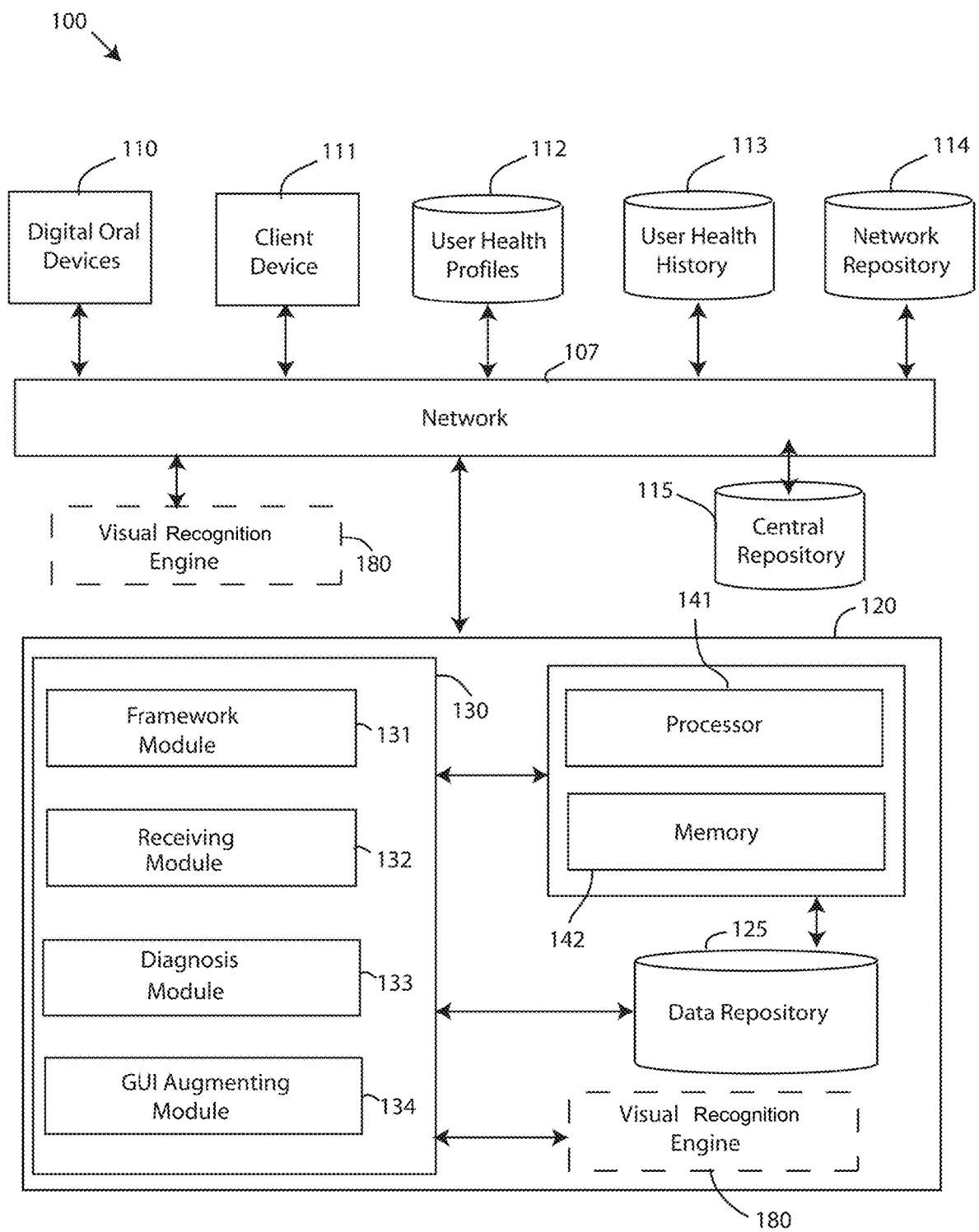
FIG. 1 depicts a block diagram of a health diagnosis system, in accordance with embodiments of the present invention.

Referring to the drawings, FIG. 1 depicts a block diagram of a health diagnosis system 100, in accordance with embodiments of the present invention. The health diagnosis system 100 is a system for instant tongue sampling and diagnosis of a current user health condition. The health diagnosis system 100 may be useful for users that want real-time feedback on the user's current health condition based on the user's tongue using a digital oral device, without the need to visit and consult a practitioner experienced with tongue diagnosis.

Embodiments of the health diagnosis system 100 may be alternatively referred to a tongue sampling system, a real-time health feedback system, a digitized oral device tongue sampling system, and the like.

The health diagnosis system 100 includes a computing system 120. Embodiments of the computing system 120 include a computer system, a computer, a server, one or more servers, a backend computing system, and the like.

Furthermore, the health diagnosis system 100 includes a plurality of digital oral devices 110, a client device 111, a user health profiles database 112, and a user health history database 113 that are communicatively coupled to the computing system 120 over a network 107. For instance, information/data is transmitted to and/or received from the plurality of digital oral devices 110, the client device 111, the user health profiles database 112, and the user health history database 113 over a network 107. In an exemplary embodiment, the network 107 is the cloud. Further embodiments of network 107 refer to a group of two or more computer systems linked together. Network 107 includes any type of computer network known by individuals skilled in the art. Examples of network 107 include a LAN, WAN, campus area networks (CAN), home area networks (HAN), metropolitan area networks (MAN), an enterprise network, cloud computing network (either physical or virtual) e.g. the Internet, a cellular communication network such as GSM or CDMA network or a mobile communications data network. In one embodiment, the architecture of the network 107 is a peer-to-peer, wherein in another embodiment, the network 107 is organized as a client/server architecture.

In an exemplary embodiment, the network 107 further comprises, in addition to the computing system 120, a connection to one or more network-accessible knowledge bases 114, which are network repositories containing information of the users preferences, user health conditions, user activity with digital oral device, tongue images, etc., network repositories or other systems connected to the network 107 that are considered nodes of the network 107. In an embodiment where the computing system 120 or network repositories allocate resources to be used by the other nodes of the network 107, the computing system 120 and network-accessible knowledge bases 114 is referred to as servers.

The network-accessible knowledge bases 114 is a data collection area on the network 107 which backs up and save all the data transmitted back and forth between the nodes of the network 107. For example, the network repository is a data center saving and cataloging the users preferences, user health conditions, user activity with digital oral device, tongue images, etc., and the like, to generate both historical and predictive reports regarding a particular user or a particular user health condition. In an exemplary embodiment, a data collection center housing the network-accessible knowledge bases 114 includes an analytic module capable of analyzing each piece of data being stored by the network-accessible knowledge bases 114. Further, the computing system 120 can be integrated with or as a part of the data collection center housing the network-accessible knowledge bases 114. In an alternative embodiment, the network-accessible knowledge bases 114 are a local repository that is connected to the computing system 120.

The plurality of digital oral devices 110 is shown as a single block in FIG. 1, but the health diagnosis system 100 includes more than one digital oral device 110. The digital oral devices 110 are digital oral devices associated with a plurality of users used to collect tongue images for building a diagnosis framework, as described in greater detail infra. The client device 111 is a digital oral device associated with a user for determining a current health condition of the user, based on the diagnosis framework built with the information/data collected from the digital oral devices 110 associated with a community of other users. In some embodiments, the client device 111 can be a combination of a digital oral device and a computing device, such as a computer, a desktop computer, a cell phone, a mobile computing device, a tablet computer, a laptop computer, a wearable computing device, a smartwatch, a media streaming device, a smart television, and the like. For instance, a digital oral device may be operated by the user to scan the user's tongue, and a user computing device may receive a current health report from the computing system 120 over network 107 based on the results of the application of the diagnosis framework. The client device 111 can include hardware functionality such as a speaker for emitting a sound, a vibration motor for creating vibrations, a display for displaying images, videos, pictorial sequences, etc., a light emitting element for emitting a light, a receiver for receiving communications, a transmitter for transmitting signals, and other similar features and hardware of a computer, smartphone, smartwatch, cell phone, tablet computer, and the like.

Figure 2:
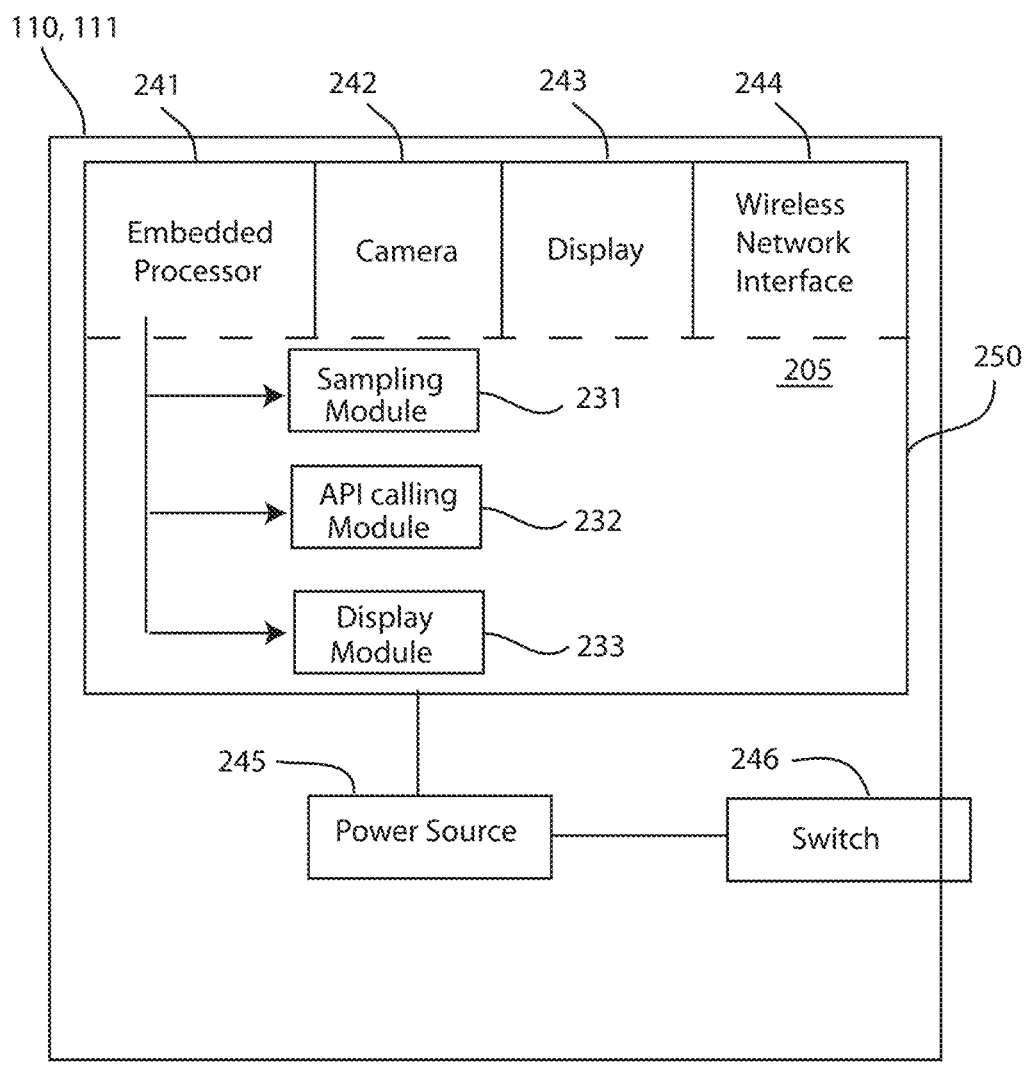
FIG. 2 depicts a block diagram of a digital oral device, in accordance with embodiments of the present invention.

FIG. 2 depicts a block diagram of a digital oral device, in accordance with embodiments of the present invention. The digital oral device (e.g. digital oral device 110 and client device 111) includes hardware and software components. The digital oral device includes a specialized integrated circuit 250. The specialized integrated circuit may be specialized and dedicated to perform only the methods described herein. Embodiments of the specialized integrated circuit may be an application specific integrated circuit (ASIC). Furthermore, embodiments of the specialized integrated circuit 250 may include an embedded processor 241, a camera 242, a display 243, and a wireless network interface 244. The digital oral device 110, 111 further includes a power source 245, such as one or more batteries. Software components of the digital oral device 110, 111 are located in a memory system 205 of the digital oral device 110, 111, or a memory system coupled to the specialized integrated circuit 250. The specialized integrated circuit 250 includes the embedded processor 241 for implementing the tasks associated with the digital oral device 110, 111. In an exemplary embodiment, the digital oral device 110, 111 communicates with the computing system 120 to transmit information/data from a tongue sampling of a user's tongue. For example, the specialized integrated circuit 250 utilizes the wireless network interface 244 for transmitting images of a tongue, over a network 107, to the computing system 120. Alternatively, the wireless network interface 244 may securely and exclusively connect to a user computing device (e.g. smartphone) associated with a user, over a short range communication network, and the user computing device can transmit the tongue images to the computing system 120. The specialized integrated circuit 250 is equipped with or coupled to a camera 242, such as a charge coupling device (CCD) imaging sensor or similar imaging sensor to detect, photograph, scan, analyze, or otherwise capture images, texture, moisture, temperature, and the like, of a user's tongue. In an exemplary embodiment, the camera 242 may be a micro digital camera. Further, the specialized integrated circuit 250 is equipped with or coupled to a display 243. The display 243 includes a graphical user interface (GUI) that displays a current health report received from the computing system 120 in response to applying the diagnosis framework to the tongue images. The display 243 can be utilized to present other information to the user, such as a last use of the digital oral device 110, 111, a time, an activity history, etc. Further, the GUI can be modified or otherwise augmented to include the customized health report and subsequent updates to the customized health report.

Moreover, the digital oral device 110, 111 includes a switch 246. The switch 246 may be partially located external to a housing of the digital oral device 110, 111. The switch 246 can be a mechanical switch, or an electromechanical switch. For instance, the switch 246 is a button accessible to the user operating the digital oral device 110, 1111, wherein if the user depresses the switch 246, the power source 245 is activated (e.g. a circuit is completed by metal-to-metal contact, or other suitable means to employ a switch to turn on a power source may be used). Activating the power source 245 provides power to the specialized integrated circuit 250, and the camera 242 can be automatically activated as power is provided to the specialized integrated circuit 250 to begin a tongue sampling procedure. By way of example, a user presses the switch 246, or a portion of the switch accessible to the user external to the housing, which powers up the specialized integrated circuit 250 to activate the camera 242 for capturing images and/or gathering real-world signals (e.g. temperature, moisture content, texture) of the user's tongue.

Additionally, the digital oral device 110, 111 includes software components, such as a sampling module 231, an API calling module 232, and a display module 233. A "module" refers to a hardware based module, software based module, or a module may be a combination of hardware and software. Hardware based modules include self-contained components such as chipsets, specialized circuitry and one or more memory devices, while a software-based module is part of a program code or linked to the program code containing specific programmed instructions, which may be loaded in the memory system 205 of the digital oral device 110, 111 and/or in a memory coupled to the specialized integrated circuit 250. A module (whether hardware, software, or a combination thereof) may be designed to implement or execute one or more particular functions or routines.

The sampling module 231 includes one or more components of hardware and/or software program code for sampling a tongue by capturing images of the tongue for analysis by the computing system 120. The sampling module 231 can activate and deactivate the camera 242 to capture one or more digital images of the tongue of the user in one or more locations of the tongue. The user can control the operation of the camera 242 by pressing switch 246 or another physical switch located on the digital oral device 110, 111.

The sampling module 231 can provide real-time feedback to the display 243 or to the user's computing device as to whether the user has sampled all of the necessary areas of the tongue. For instance, as images are captured, the sampling module 231 can determine whether all tongue areas have been sufficiently detected by the user's operation of the digital oral device 110, 111. Alternatively, the sampling module 231 may initially locate an oral device spatial position in the user's mouth by scanning the interior of the user's mouth, and use the spatial location of the device 110, 111 to track whether the user has manipulated the device 110, 111 to capture all areas of the tongue. In an exemplary embodiment, the sampling module 231 uses both techniques to determine that the necessary areas of the tongue have been captured. Moreover, the sampling module 231 can establish a connection or link between the digital oral device 110, 111 and the user computing device, using the wireless network interface 244. The link between the digital oral device 110, 111 and the user computing device may be established using Bluetooth® technology, near field communication (NFC), and/or a combination thereof.

The API module 232 includes one or more components of hardware and/or software program code for communicating with the computing system 120 over network 107 to transmit tongue images and potentially other tongue data for health analysis. For example, the API calling module 232 calls SaaS API and uploads the tongue samples (e.g. images) to the computing system 120 for application of the diagnosis framework to determine a current health condition of the user.

The display module 233 includes one or more components of hardware and/or software program code for displaying custom health report form indicative of the current health condition of the user. In some embodiments, the digital oral device 110, 111 receives the custom health report directly from the computing system 120, and the display module 233 displays the report on the display 243. In other embodiment, the custom health report is received by a linked user computing device, and the user computing device directly displays the results, or sends the data regarding the custom health report to the digital oral device 110, 111 over the short range communication network linking the user computing device and the display module 233 displays the report on display 243.

Figure 3:
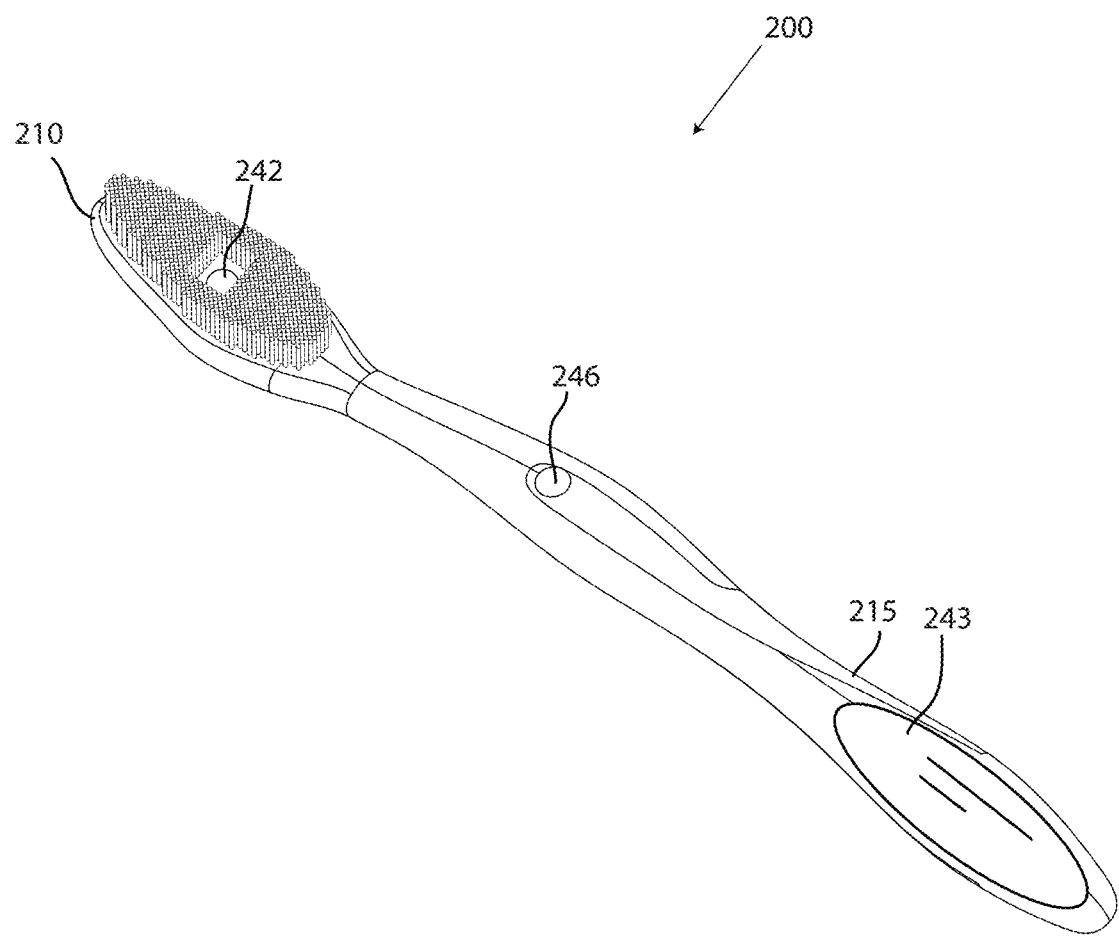
FIG. 3 depicts a perspective view of a digital oral device, in accordance with embodiments of the present invention.

FIG. 3 depicts a perspective view of a digital oral device, in accordance with embodiments of the present invention. In an exemplary embodiment, the digital oral device 110, 111 is a smart toothbrush 200. The smart toothbrush 200 includes a head portion 210 and a body portion 215. The head portion 210 includes bristles as those of a conventional toothbrush. Located between the bristles is a camera 242 for capturing the tongue images, as described above. While one camera 242 is shown in the illustrated embodiment, the smart toothbrush 200 can include more than one camera 242 positioned on the head portion 210 for maximizing a coverage of the user's tongue. The body portion 215 of the smart toothbrush 200 includes display 243 and switch 246. The head portion 210 and the body portion 215 are sized and dimensioned similar to a conventional toothbrush; however, the overall size, design, shape, etc. can vary to accommodate various needs, designs, applications, and the like. Furthermore, the smart toothbrush 200 can include one or more sensors in addition to the camera 242, coupled to the integrated circuit 250. The one or more sensors can include a temperature sensor for detecting a temperature of the tongue and/or the interior of the mouth of the user, a moisture sensor for detecting a moisture level of the tongue's surface, and other sensor for obtaining physical characteristics of the tongue. Further, the smart toothbrush 200 may require ultra-low processing requirements to operate the smart toothbrush 200. The low processing power requirement along with limited hardware components, allows the manufacture of the smart toothbrush 200 to be relatively inexpensive. The smart toothbrush 200 may be comprised of inexpensive material, such as plastic, for large scale, low-cost distribution. In some embodiments, the entire housing of the smart toothbrush 200 is comprised of plastic. Other materials can be used in combination with plastic or without plastic to form the smart toothbrush 200.

Referring back to FIG. 1, the health diagnosis system 100 includes a user health profiles database 112. The user health profiles database 112 is a database or other storage device that includes user personal characteristic information, the user personal characteristic information including an age, an eating habit, a working condition, a known health condition, a medical history, a body temperature, and a current health of the user. The personal characteristic information stored in the database is collected when users operate the digital oral device 110 to transmit a plurality of tongue images to the computing system 120. For instance, each user creates a profile that is stored on the user health profiles database 112. The user profile information includes user identifying information, user preferences, eating habits, dietary information, past health reports generated by the computing system 120, sensor data, and the like. The user health profiles database 112 stores data on all the users in the system to help develop the diagnosis framework. Furthermore, the health diagnosis system 100 includes a user health history database 113. The user health history database 113 is a database or other storage device that includes health information specific to an individual user. The health information includes a history of health conditions, past health reports, activity information of the user, and the like.

Furthermore, the computing system 120 of the health diagnosis system 100 is equipped with a memory device 142 which stores various data/information/code, and a processor 141 for implementing the tasks associated with the health diagnosis system 100. A health diagnosis application 130 is loaded in the memory device 142 of the computing system 120. The health diagnosis application 130 can be an interface, an application, a program, a module, or a combination of modules. In an exemplary embodiment, the health diagnosis application 130 is a software application running on one or more back end servers (e.g. computing system 120), servicing the digital oral devices 110 and the client device 111.

The health diagnosis application 130 of the computing system 120 includes a framework module 131, a receiving module 132, a diagnosis module 133, and a GUI augmenting module 134. A "module" refers to a hardware-based module, a software-based module, or a module that is a combination of hardware and software. Hardware-based modules include self-contained components such as chipsets, specialized circuitry and one or more memory devices, while a software-based module is a part of a program code or linked to the program code containing specific programmed instructions, which is loaded in the memory device of the computing system 120. A module (whether hardware, software, or a combination thereof) is designed to implement or execute one or more particular functions or routines.

The framework module 131 includes one or more components of hardware and/or software program code for acquiring a plurality of tongue images from a plurality of digital oral devices 110 associated with a plurality of users, and a current health condition of the plurality of users. As each user that has created a profile and is using the digital oral device 110, the images of the tongues are collected and stored in the user health profile database 112. The health condition of the user using the digital oral device 110 is also obtained from the user or determined by the framework module 131. For example, the user health condition can be obtained from the user inputting health information into the user's profile. In an exemplary embodiment, the current health condition of the plurality of users is acquired by accessing user health profiles that contain user personal characteristic information, the user personal characteristic information including an age, an eating habit, a working condition, a known health condition, a medical history, a body temperature, and a current health. The user health profiles can be created by information provided by a user (e.g. current pain or symptoms experienced by the user), a user's wearable device (e.g. smartwatch sharing heart health information), a fitness application (e.g. exercise activity), a food diary application (e.g. user's eating habits), a personal diet application (e.g. current participation in a weight loss program), a medical record (e.g. diagnosed health conditions), a sleep tracking device (e.g. average hours of sleep per night), a drug prescription history (e.g. current medications used by the user), and the like. The multiple data sources can be used to determine a current health condition of the user, which is used in conjunction with the plurality of tongue images to build a diagnosis framework over time to be applied to subsequently received tongue images for real-time diagnosis of a current health condition of a user.

The framework module 131 builds the diagnosis framework by analyzing the collected tongue images with a visual recognition engine 180 to determine tongue characteristics of each tongue captured in the tongue images, and correlating the tongue characteristics with the current health condition of the user. For instance, the framework module 131 employs the visual recognition engine 180 to extract or classify one or more tongue characteristics from the image(s) of the tongue received from the digital oral device 110 associated with a user. Tongue characteristics include a tongue color, a tongue coating, a tongue appearance, a tongue shape, a tongue texture, a tongue wetness, a tongue dryness, and a tongue temperature. By way of example, the visual recognition engine 180 classifies one or more images of a tongue as: i) the color of the tongue is pink, not pale, scarlet, or red, ii) the pink tongue color is consistent across the entire tongue, iii) small cylindrical taste buds are located on the entire top surface of the tongue, iv) the tongue appears more wet than dry, v) no cracks are detected on the surface of the tongue, vi) thick white mucus coating is present on the surface of the tongue, and vii) no teeth marks are detected on the tongue. The framework module 131 correlates the tongue characteristics with the health condition of the user to define a relationship between tongue characteristics and health. For example, if the user is currently healthy and not experiencing any pain or symptoms of a medical condition, the framework module 131 correlates the tongue characteristics with a positive or normal health condition. If the user is currently experiencing stomach pains, the framework module 131 correlates the tongue characteristics with a health condition relating to a stomach. If the user is currently experiencing a headache, the framework module 131 correlates the tongue characteristics with a health condition relating to a headache.

As additional samples come in from other users, the framework module 131 learns over time which tongue characteristics correlate to specific illnesses, symptoms, conditions, etc. For instance, a tongue image that shows a red tongue with a higher dryness level correlates to a first health condition, while a tongue image that shows a red tongue level with a higher wetness level correlates to a second health condition. Machine learning algorithms are used to continuously build and improve the diagnosis framework for diagnosis health conditions based on received sample tongue images. The framework module 131 stores the diagnosis framework in a central repository 115. The central repository 115 is updated over time as additional tongue images are received from additional users.

Referring still to FIG. 1, the computing system 120 includes a receiving module 132. The receiving module 132 includes one or more components of hardware and/or software program code for receiving an image of a tongue of the user to be diagnosed from the client device 111 (e.g. digital oral device) associated with the user to be diagnosed. For instance, the client device 111 transmits one or more images of the user's tongue to the computing system 120 for real-time diagnosis of the user's health. The user to be diagnosed operates the client device 111 by inserting the client device 111 into the mouth of the user to extract images and potential other sensor data. The receiving module 132 receives the image data and potential sensor data from the client device 111, which can be a digital oral device or a user computing system, as described supra.

The computing system 120 also includes a diagnosis module 133. The diagnosis module 133 includes one or more components of hardware and/or software program for identifying tongue characteristics from the image of the tongue of the user to be diagnosed using the visual image recognition engine 180. The diagnosis module 133 employs the visual recognition engine 180 to extract or classify one or more tongue characteristics from the image(s) of the tongue received from the digital oral device associated with a user to be diagnosed (i.e. client device 111). By way of example, the visual recognition engine 180 classifies one or more images of a tongue as: i) the color of the tongue is scarlet, not pale, pink, or red, ii) the pink tongue color is inconsistent across the entire tongue, iii) small cylindrical taste buds are located on the entire top surface of the tongue, iv) the tongue appears more dry than wet, v) no cracks are detected on the surface of the tongue, vi) thin white mucus coating is present on the surface of the tongue, and vii) no teeth marks are detected on the tongue.

In response to identifying the tongue characteristics, the diagnosis module 133 applies the diagnosis framework to the tongue characteristics of the tongue to diagnosis the current health condition of the user. The diagnosis module 133 accesses the diagnosis framework from the central repository 115 and inputs the tongue characteristics to the diagnosis framework to receive a diagnosis of current health condition of the user based on the results of the application of the diagnosis framework to the identified tongue characteristics. Based on the application of the diagnosis framework to the tongue characteristics, the framework module 133 can determine a health report that is customized to the individual user operating the client device 111.

Referring back to FIG. 1, the computing system 120 includes GUI augmenting module 134. The GUI augmenting module 134 includes one or more components of hardware and/or software program for modifying a graphical user interface of the digital oral device (e.g. client device 111) to display the custom health report indicative of the current health condition of the user, in response to applying the diagnosis framework. For instance, the GUI augmenting module 134 modifies the GUI of the client device 111 so that the user is presented with real-time analysis of the user's health condition based on tongue characteristics. Further, the GUI augmenting module 134 can filter the diagnosis of the current health condition of the user to account for a known user health condition, prior to the initially modifying the graphical user interface to display the custom health report. For example, a prior user health condition can affect the actual health condition of the user output as a result of the diagnosis framework. By filtering the initial results of the diagnosis framework application, the custom health report can be adjusted to account for known user health, which can improve an overall accuracy of the report.

The client device 111 can be used on a daily basis to receive daily customized health reports, in real-time by sampling the user's tongue. As a result, the GUI augmentation module 134 augments the graphical user interface of the digital oral device to update the custom health report in response to receiving an additional image of the tongue of the user from the digital oral device. The custom reports can be tracked and monitored over time to formulate suggested changes to a user's eating habits, sleeping schedules, fitness activity, and the like, which can be used to increase an overall health of the user.

Figure 4:
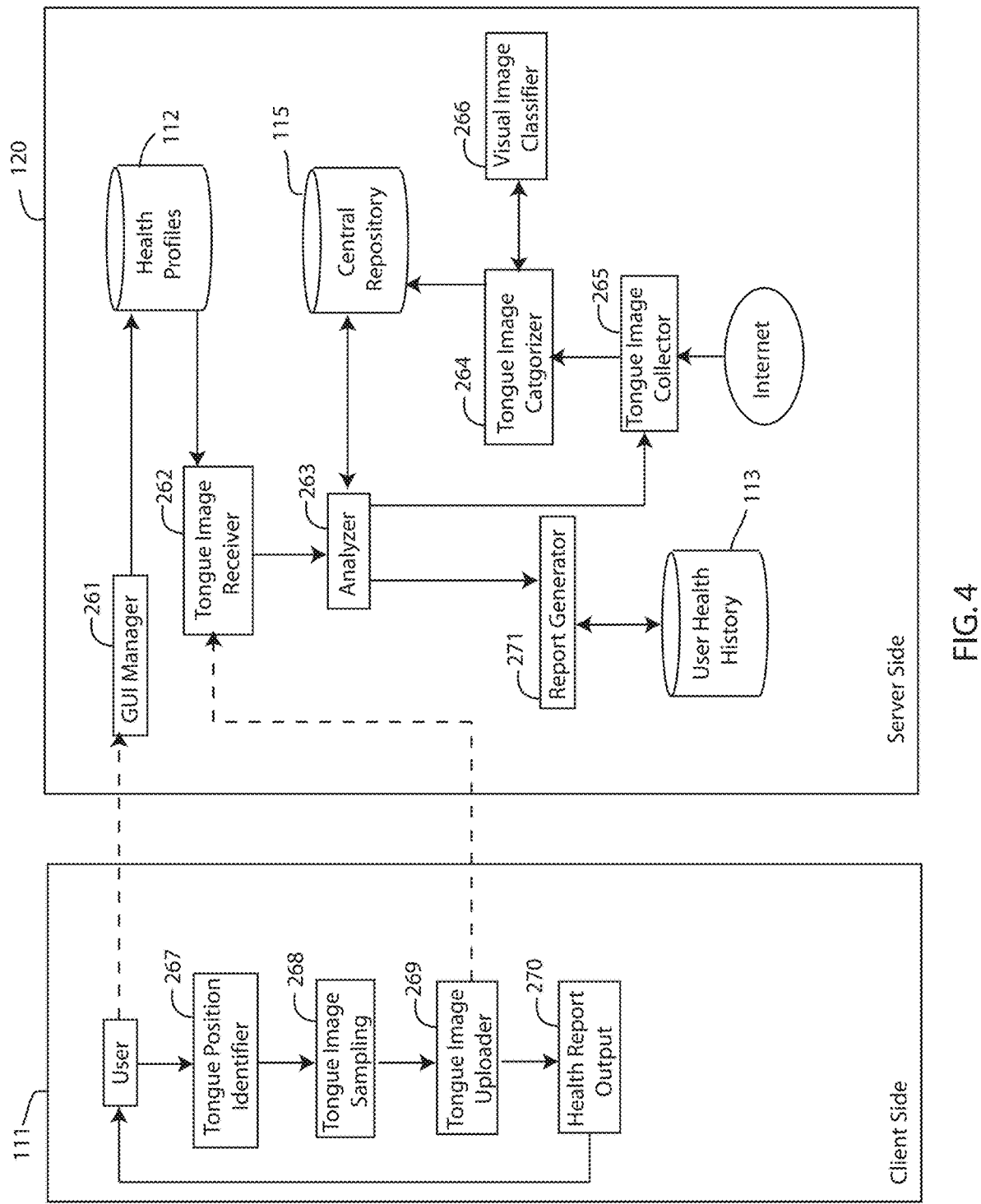
FIG. 4 depicts a client-side and a server-side block diagram of the health diagnosis system, in accordance with embodiments of the present invention.

FIG. 4 depicts a client-side and a server-side block diagram of the health diagnosis system 100, in accordance with embodiments of the present invention. The client-side is represented by operations performed by the client device 111 and the server-side is represented by operating performed the computing system 120. The user interacts with the GUI manager 251 to input and configure personal information regarding the user which is stored in the user health profiles database 112. The health profiles database 112 includes user personal characteristic information, the user personal characteristic information including an age, an eating habit, a working condition, a known health condition, a medical history, a body temperature, and a current health. On the client-side, the client device 111 is used by the user to identify a tongue position with a tongue position identifier 267 and sample the user's tongue with tongue image sampling 268. The tongue image uploader 269 of the client device 111 uploads the tongue images over network 107 to the tongue image receiver 262 of the server-side. The server-side analyzes the tongue images by applying the framework stored in the central repository 115. The diagnosis framework stored in the central repository 115 is built using the tongue image collector 265, the tongue image categorizer 264, and a visual image classifier 266. The tongue image collector 265 collects the tongue images from the plurality of users operating digital oral devices 110. The tongue image categorizer 264 categorizes different tongue diagnosis templates based on known user health conditions, symptoms, medical history, etc., correlated to the tongue characteristics detected from the images extracted by the visual image classifier 266. Further, on the server-side, the tongue image(s) received from the client device 111 is analyzed by analyzer 263 using the diagnosis framework to generate a custom health report by the report generator 271 for the user operating the client device 111. The custom health report can be adjusted by a filtering process that takes the user health history into account, accessing the user health history from the user health history database 113. The server-side then modifies the GUI of the client device 111 to display the unique health report via the health report output 270, and updates the GUI accordingly in view of additional tongue images received from the client device 111.

Various tasks and specific functions of the modules of the computing system 120 may be performed by additional modules, or may be combined into other module(s) to reduce the number of modules. Further, an embodiment of the computer or computer system 120 comprises specialized, non-generic hardware and circuitry (i.e., specialized discrete non-generic analog, digital, and logic-based circuitry) (independently or in combination) particularized for executing only methods of the present invention. The specialized discrete non-generic analog, digital, and logic-based circuitry includes proprietary specially designed components (e.g., a specialized integrated circuit, such as for example an Application Specific Integrated Circuit (ASIC), designed for only implementing methods of the present invention).

Furthermore, the health diagnosis system 100 uses specific rules to build a framework for providing a real-time tongue sampling diagnosis to a user. The specific rules are applied to tongue characteristics obtained from a specialized device (e.g. smart toothbrush) to build the framework. The framework is applied to unique and individualized tongue characteristics of a particular user, such that the results of the diagnosis are tailored to an individual user's tongue characteristics. The GUI of the specialized device is modified or otherwise augmented to present the custom results to the user. Without applying the specific set of rules and building a framework, a user could not receive real-time feedback in response to a tongue sampling. The health diagnosis system 100 provides a technical solution by augmenting GUIs of specialized devices based on a set of rules used to build a unique diagnosis framework.

Figure 5:
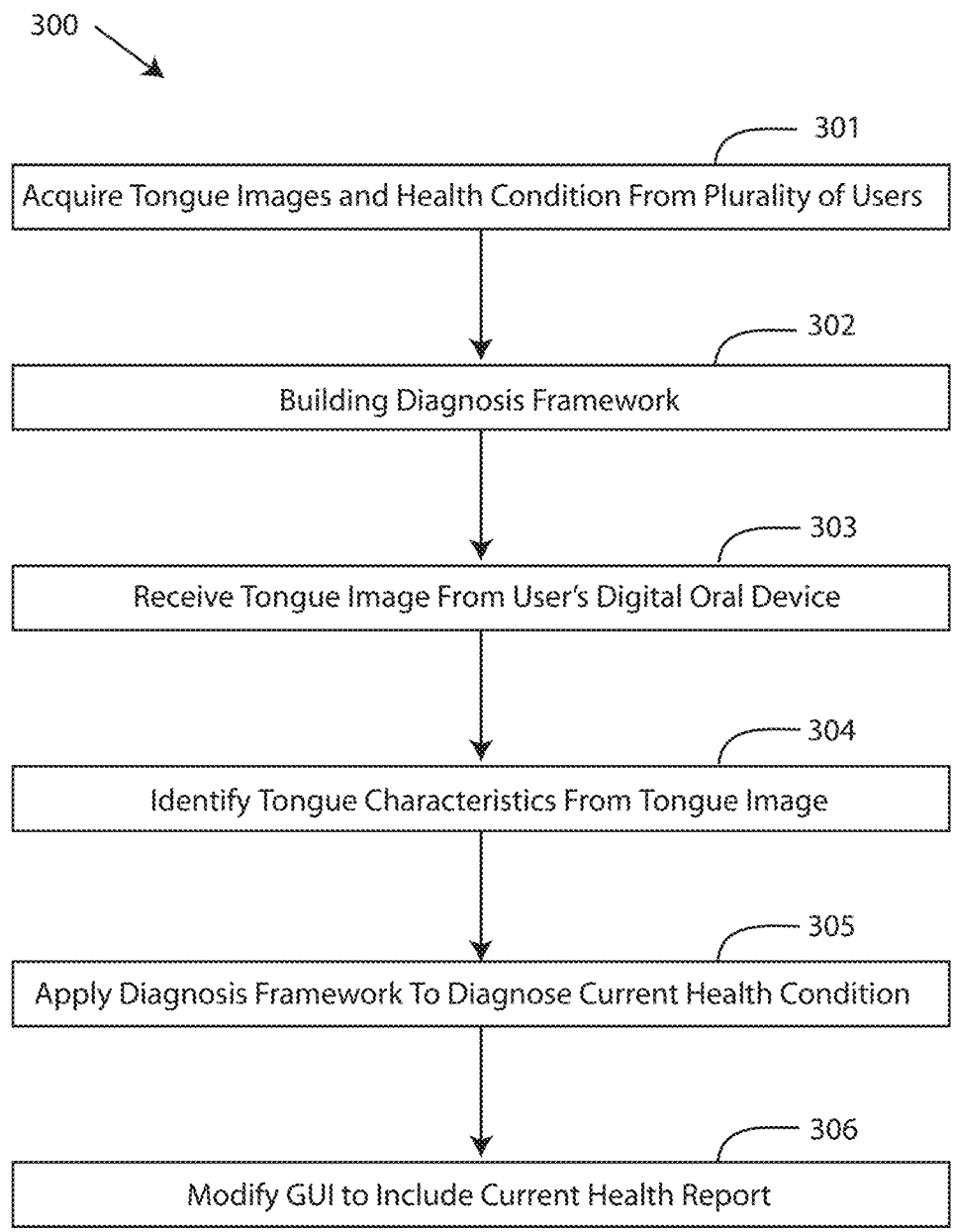
FIG. 5 depicts a flow chart of a method for instant tongue sampling and diagnosis, in accordance with embodiments of the present invention.

Referring now to FIG. 5, which depicts a flow chart of a method 300 for instant tongue sampling and diagnosis, in accordance with embodiments of the present invention. One embodiment of a method 300 or algorithm that may be implemented for instant tongue sampling and diagnosis with the health diagnosis system 100 described in FIGS. 1-4 using one or more computer systems as defined generically in FIG. 7 below, and more specifically by the specific embodiments of FIG. 1.

Embodiments of the method 300 for instant tongue sampling and diagnosis, in accordance with embodiments of the present invention, may begin at step 301 wherein tongue images and health conditions of users are acquired from a plurality of users operating digital oral devices. Step 302 builds a diagnosis framework. Step 303 receives tongue images from a user's digital oral device. Step 304 identifies tongue characteristics from the tongue images received from the user. Step 305 applies the diagnosis framework to diagnose a current health condition of the user. Step 306 modifies the GUI of the user digital oral device to include the current health report.

Figure 6:
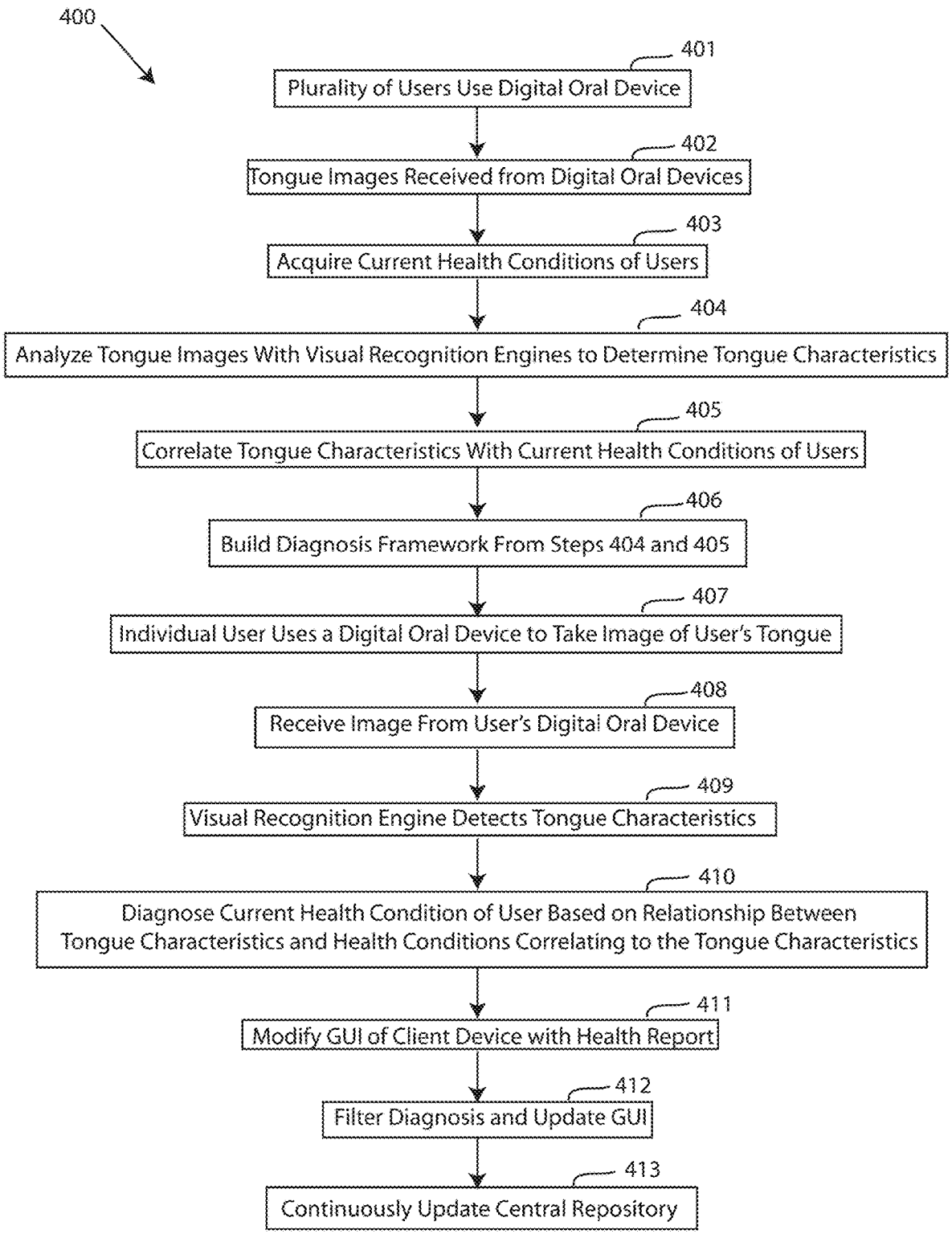
FIG. 6 depicts a detailed flow chart of a method for instant tongue sampling and diagnosis, in accordance with embodiments of the present invention.

FIG. 6 depicts a detailed flow chart of a method 400 for instant tongue sampling and diagnosis, in accordance with embodiments of the present invention. At step 401, a plurality of users use a digital oral device. At step 402, tongue images are received from the digital oral devices used by the plurality of users in step 401. At step 403, current health conditions of the plurality of users from step 401 are acquired. At step 404, the tongue images received in step 402 are analyzed with a visual recognition engine to determine tongue characteristics. At step 405, the tongue characteristics determined in step 404 are correlated with the health condition of the users acquired in step 403. At step 406, a diagnosis framework is built from the outputs of steps 404 and 405. At step 407, an individual user uses a digital oral device to take images of the user's tongue, which are received at step 408. At step 409, the visual recognition engine detects tongue characteristics from the images received at step 408. At step 410, a current health condition is diagnosed based on the relationship between the tongue characteristics of the user's tongue and the health conditions correlating to the specific tongue characteristics. At step 411, a GUI of the user digital oral device used in step 407 is modified to include a custom health report that includes the diagnosis. At step 412, the diagnosis is filtered and the GUI is augmented to account for the filtering process. At step 413, the diagnosis framework, which is stored in a central repository, is continuously updated as new tongue sample data is received.

Figure 7:
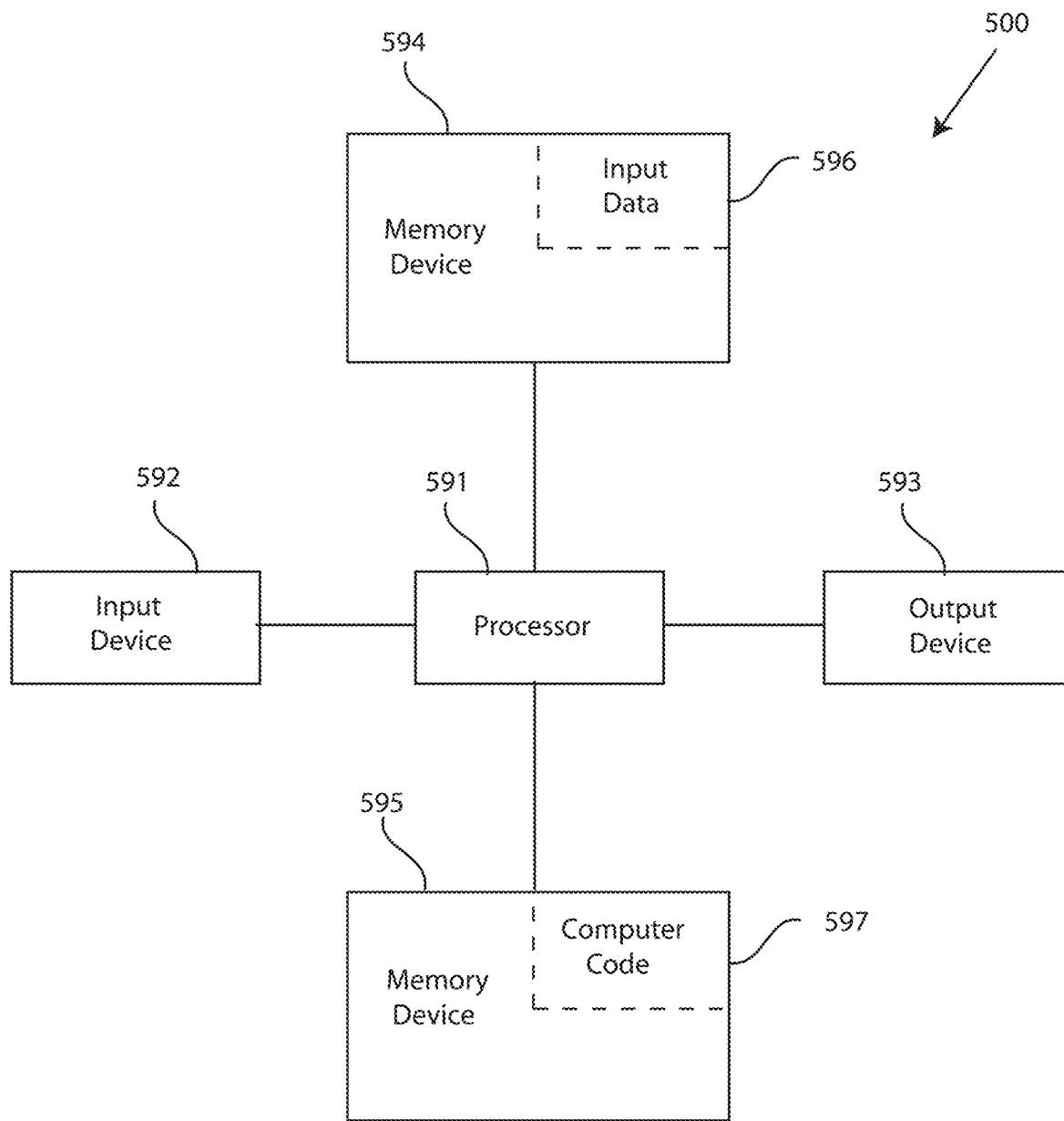
FIG. 7 depicts a block diagram of a computer system for a health diagnosis system of FIGS. 1-4, capable of implementing a method for instant tongue sampling and diagnosis of FIGS. 5-6, in accordance with embodiments of the present invention.

FIG. 7 depicts a block diagram of a computer system for the health diagnosis system 100 of FIGS. 1-4, capable of implementing methods for instant tongue sampling and diagnosis of FIGS. 5-6, in accordance with embodiments of the present invention. The computer system 500 may generally comprise a processor 591, an input device 592 coupled to the processor 591, an output device 593 coupled to the processor 591, and memory devices 594 and 595 each coupled to the processor 591. The input device 592, output device 593 and memory devices 594, 595 may each be coupled to the processor 591 via a bus. Processor 591 may perform computations and control the functions of computer system 500, including executing instructions included in the computer code 597 for the tools and programs capable of implementing a method for instant tongue sampling and diagnosis in the manner prescribed by the embodiments of FIGS. 5-6 using the health diagnosis system 100 of FIGS. 1-4, wherein the instructions of the computer code 597 may be executed by processor 591 via memory device 595. The computer code 597 may include software or program instructions that may implement one or more algorithms for implementing the method for instant tongue sampling and diagnosis, as described in detail above. The processor 591 executes the computer code 597. Processor 591 may include a single processing unit, or may be distributed across one or more processing units in one or more locations (e.g., on a client and server).

The memory device 594 may include input data 596. The input data 596 includes any inputs required by the computer code 597. The output device 593 displays output from the computer code 597. Either or both memory devices 594 and 595 may be used as a computer usable storage medium (or program storage device) having a computer-readable program embodied therein and/or having other data stored therein, wherein the computer-readable program comprises the computer code 597. Generally, a computer program product (or, alternatively, an article of manufacture) of the computer system 500 may comprise said computer usable storage medium (or said program storage device).

Memory devices 594, 595 include any known computer-readable storage medium, including those described in detail below. In one embodiment, cache memory elements of memory devices 594, 595 may provide temporary storage of at least some program code (e.g., computer code 597) in order to reduce the number of times code must be retrieved from bulk storage while instructions of the computer code 597 are executed. Moreover, similar to processor 591, memory devices 594, 595 may reside at a single physical location, including one or more types of data storage, or be distributed across a plurality of physical systems in various forms. Further, memory devices 594, 595 can include data distributed across, for example, a local area network (LAN) or a wide area network (WAN). Further, memory devices 594, 595 may include an operating system (not shown) and may include other systems not shown in FIG. 7.

In some embodiments, the computer system 500 may further be coupled to an Input/output (I/O) interface and a computer data storage unit. An I/O interface may include any system for exchanging information to or from an input device 592 or output device 593. The input device 592 may be, inter alia, a keyboard, a mouse, etc. or in some embodiments the touchscreen of a computing device. The output device 593 may be, inter alia, a printer, a plotter, a display device (such as a computer screen), a magnetic tape, a removable hard disk, a floppy disk, etc. The memory devices 594 and 595 may be, inter alia, a hard disk, a floppy disk, a magnetic tape, an optical storage such as a compact disc (CD) or a digital video disc (DVD), a dynamic random access memory (DRAM), a read-only memory (ROM), etc. The bus may provide a communication link between each of the components in computer 500, and may include any type of transmission link, including electrical, optical, wireless, etc.

An I/O interface may allow computer system 500 to store information (e.g., data or program instructions such as program code 597) on and retrieve the information from computer data storage unit (not shown). Computer data storage unit includes a known computer-readable storage medium, which is described below. In one embodiment, computer data storage unit may be a non-volatile data storage device, such as a magnetic disk drive (i.e., hard disk drive) or an optical disc drive (e.g., a CD-ROM drive which receives a CD-ROM disk). In other embodiments, the data storage unit may include a knowledge base or data repository 125 as shown in FIG. 1.

As will be appreciated by one skilled in the art, in a first embodiment, the present invention may be a method; in a second embodiment, the present invention may be a system; and in a third embodiment, the present invention may be a computer program product. Any of the components of the embodiments of the present invention can be deployed, managed, serviced, etc. by a service provider that offers to deploy or integrate computing infrastructure with respect to instant tongue sampling and diagnosis. Thus, an embodiment of the present invention discloses a process for supporting computer infrastructure, where the process includes providing at least one support service for at least one of integrating, hosting, maintaining and deploying computer-readable code (e.g., program code 597) in a computer system (e.g., computer system 500) including one or more processor(s) 591, wherein the processor(s) carry out instructions contained in the computer code 597 causing the computer system to provide instant tongue sampling and diagnosis. Another embodiment discloses a process for supporting computer infrastructure, where the process includes integrating computer-readable program code into a computer system 500 including a processor.

The step of integrating includes storing the program code in a computer-readable storage device of the computer system 500 through use of the processor. The program code, upon being executed by the processor, implements a method for instant tongue sampling and diagnosis. Thus, the present invention discloses a process for supporting, deploying and/or integrating computer infrastructure, integrating, hosting, maintaining, and deploying computer-readable code into the computer system 500, wherein the code in combination with the computer system 500 is capable of performing a method for instant tongue sampling and diagnosis.

A computer program product of the present invention comprises one or more computer-readable hardware storage devices having computer-readable program code stored therein, said program code containing instructions executable by one or more processors of a computer system to implement the methods of the present invention.

A computer system of the present invention comprises one or more processors, one or more memories, and one or more computer-readable hardware storage devices, said one or more hardware storage devices containing program code executable by the one or more processors via the one or more memories to implement the methods of the present invention.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine-dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer-implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 8:
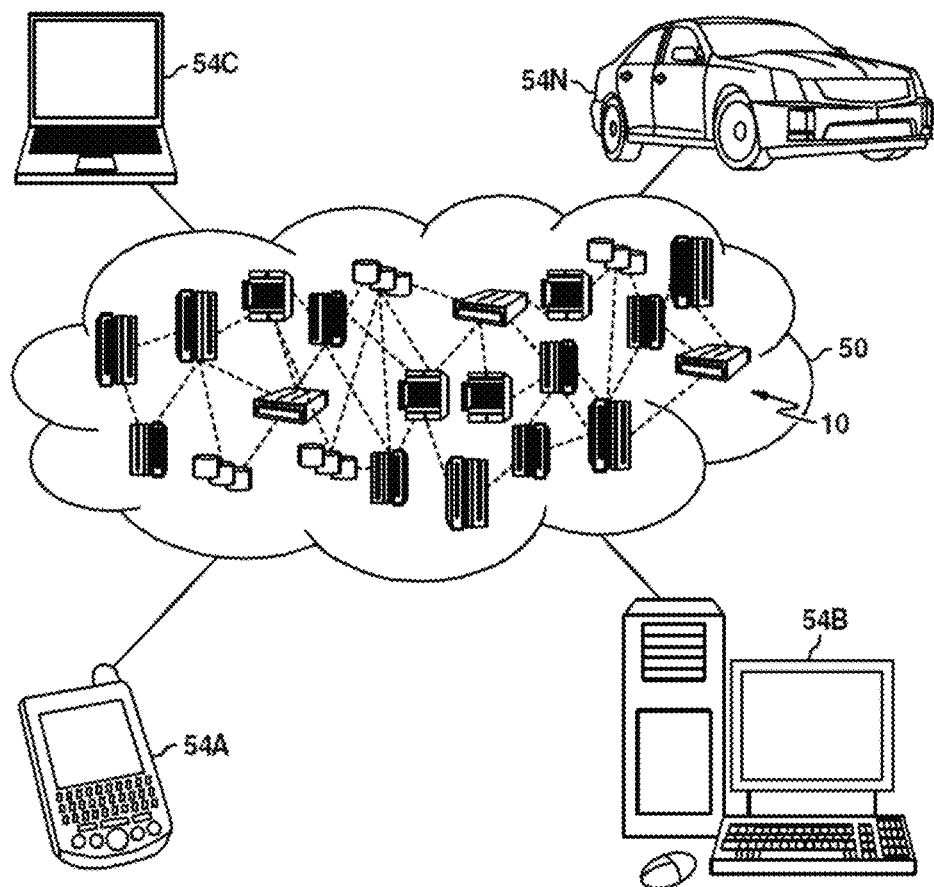
FIG. 8 depicts a cloud computing environment, in accordance with embodiments of the present invention.

Referring now to FIG. 8, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A, 54B, 54C and 54N shown in FIG. 8 are intended to be illustrative only and that computing nodes 10 and cloud computing environment 50 can communicate with any type of computerized device over any type of network and/or network addressable connection (e.g., using a web browser).

Figure 9:
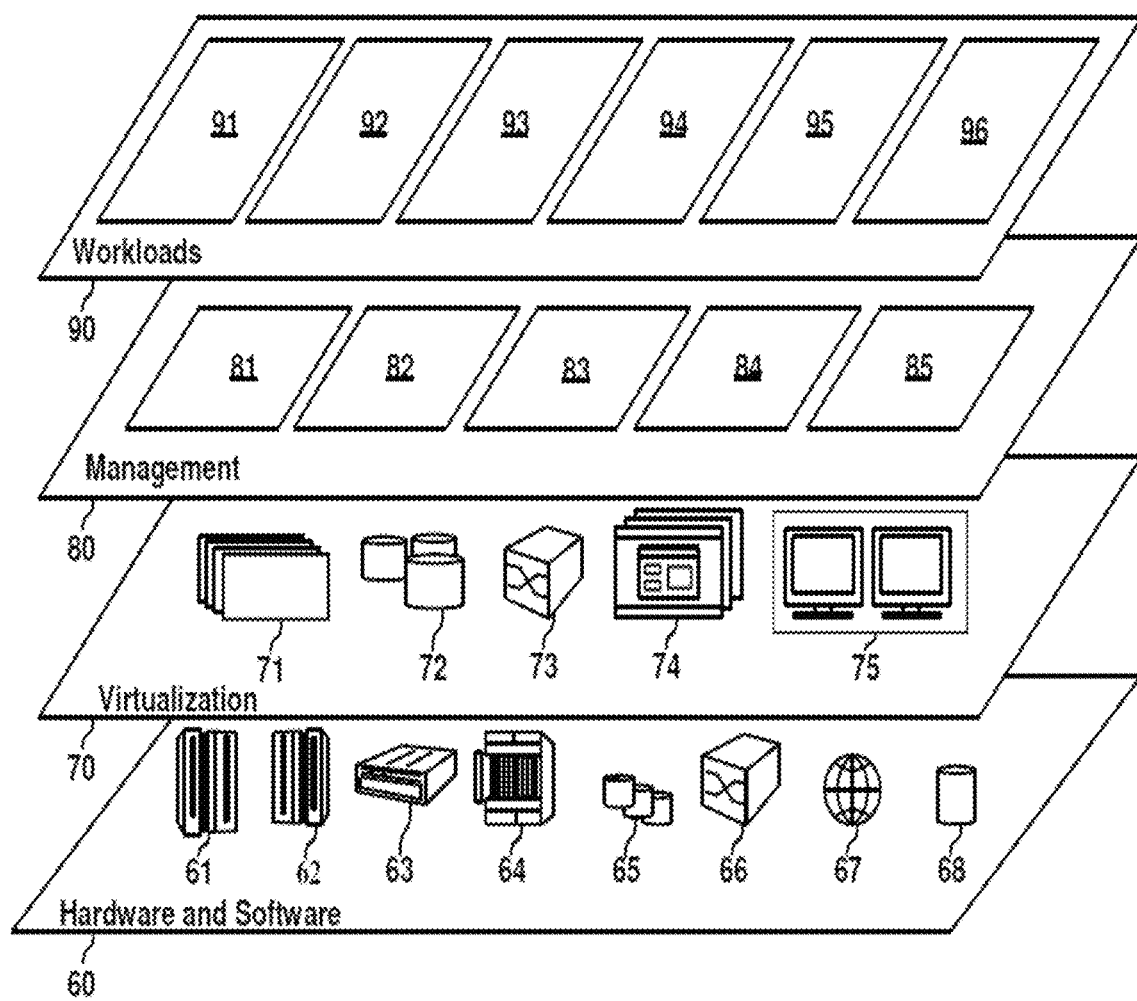
FIG. 9 depicts abstraction model layers, in accordance with embodiments of the present invention.

Referring now to FIG. 9, a set of functional abstraction layers provided by cloud computing environment 50 (see FIG. 8) are shown. It should be understood in advance that the components, layers, and functions shown in FIG. 9 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and GUI and instant tongue sampling and diagnosis 96.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
    acquiring, by a processor of a computing system, a plurality of tongue images from a plurality of digital oral devices associated with a plurality of users, and a current health condition of the plurality of users, wherein the digital oral devices provide feedback to a display of the digital oral device as to whether all tongue areas have been detected by a user's operation of the digital oral device;
    building, by the processor, a diagnosis framework for diagnosing a current health condition of a user by: i) analyzing the collected tongue images with a visual recognition engine to determine tongue characteristics of each tongue captured in the tongue images, and ii) correlating the tongue characteristics with the current health condition;
    receiving, by the processor, an image of a tongue of the user from a digital oral device associated with the user;
    identifying, by the processor, tongue characteristics from the image of the tongue using the visual image recognition engine;
    applying, by the processor, the diagnosis framework to the tongue characteristics of the tongue to diagnosis the current health condition of the user; and
    modifying, by the processor, a graphical user interface of the digital oral device to display a custom health report indicative of the current health condition of the user, in response to applying the diagnosis framework.

2. The method of claim 1, wherein the current health condition of the plurality of users is acquired by accessing user health profiles that contain user personal characteristic information, the user personal characteristic information including an age, an eating habit, a working condition, a known health condition, a medical history, a body temperature, and a current health.

3. The method of claim 1, wherein the correlating defines a relationship between tongue characteristics and health.

4. The method of claim 1, further comprising: augmenting, by the processor, the graphical user interface of the digital oral device to update the custom health report in response to receiving an additional image of the tongue of the user from the digital oral device.

5. The method of claim 1, further comprising: filtering, by the processor, the diagnosis of the current health condition of the user to account for a known user health condition, prior to the modifying the graphical user interface to display the custom health report.

6. The method of claim 1, further comprising: storing, by the processor, the diagnosis framework in a central repository, wherein the central repository is updated over time as additional tongue images are received from additional users.

7. The method of claim 1, wherein the digital oral device is a toothbrush including at least one camera positioned on a head of the toothbrush, a display on a body of the toothbrush, and a wireless network interface for connecting to the computing system over a network.

8. A computing system, comprising:
    a processor;
    a memory device coupled to the processor; and
    a computer readable storage device coupled to the processor, wherein the storage device contains program code executable by the processor via the memory device to implement a method for instant tongue sampling and diagnosis, the method comprising:
    acquiring, by the processor, a plurality of tongue images from a plurality of digital oral devices associated with a plurality of users, and a current health condition of the plurality of users, wherein the digital oral devices provide feedback to a display of the digital oral device as to whether all tongue areas have been detected by a user's operation of the digital oral device;
    building, by the processor, a diagnosis framework for diagnosing a current health condition of a user by: i) analyzing the collected tongue images with a visual recognition engine to determine tongue characteristics of each tongue captured in the tongue images, and ii) correlating the tongue characteristics with the current health condition;
    receiving, by the processor, an image of a tongue of the user from a digital oral device associated with the user;

identifying, by the processor, tongue characteristics from the image of the tongue using the visual image recognition engine;

applying, by the processor, the diagnosis framework to the tongue characteristics of the tongue to diagnosis the current health condition of the user; and modifying, by the processor, a graphical user interface of the digital oral device to display a custom health report indicative of the current health condition of the user, in response to applying the diagnosis framework.

9. The computing system of claim 8, wherein the current health condition of the plurality of users is acquired by accessing user health profiles that contain user personal characteristic information, the user personal characteristic information including an age, an eating habit, a working condition, a known health condition, a medical history, a body temperature, and a current health.

10. The computing system of claim 8, wherein the correlating defines a relationship between tongue characteristics and health.

11. The computing system of claim 8, further comprising: augmenting, by the processor, the graphical user interface of the digital oral device to update the custom health report in response to receiving an additional image of the tongue of the user from the digital oral device.

12. The computing system of claim 8, further comprising: filtering, by the processor, the diagnosis of the current health condition of the user to account for a known user health condition, prior to the modifying the graphical user interface to display the custom health report.

13. The computing system of claim 8, further comprising: storing, by the processor, the diagnosis framework in a central repository, wherein the central repository is updated over time as additional tongue images are received from additional users.

14. The computing system of claim 8, wherein the digital oral device is a toothbrush including at least one camera positioned on a head of the toothbrush, a display on a body of the toothbrush, and a wireless network interface for connecting to the computing system over a network.

15. A computer program product, comprising a computer readable hardware storage device storing a computer readable program code, the computer readable program code comprising an algorithm that when executed by a computer processor of a computing system implements a method for instant tongue sampling and diagnosis, the method comprising:

acquiring, by a processor of a computing system, a plurality of tongue images from a plurality of digital oral devices associated with a plurality of users, and a current health condition of the plurality of users, wherein the digital oral devices provide feedback to a display of the digital oral device as to whether all tongue areas have been detected by a user's operation of the digital oral device;

building, by the processor, a diagnosis framework for diagnosing a current health condition of a user by: i) analyzing the collected tongue images with a visual recognition engine to determine tongue characteristics of each tongue captured in the tongue images, and ii) correlating the tongue characteristics with the current health condition;

receiving, by the processor, an image of a tongue of the user from a digital oral device associated with the user;

identifying, by the processor, tongue characteristics from the image of the tongue using the visual image recognition engine;

applying, by the processor, the diagnosis framework to the tongue characteristics of the tongue to diagnosis the current health condition of the user; and modifying, by the processor, a graphical user interface of the digital oral device to display a custom health report indicative of the current health condition of the user, in response to applying the diagnosis framework.

16. The computer program product of claim 15, wherein the current health condition of the plurality of users is acquired by accessing user health profiles that contain user personal characteristic information, the user personal characteristic information including an age, an eating habit, a working condition, a known health condition, a medical history, a body temperature, and a current health.

17. The computer program product of claim 15, further comprising: augmenting, by the processor, the graphical user interface of the digital oral device to update the custom health report in response to receiving an additional image of the tongue of the user from the digital oral device.

18. The computer program product of claim 15, further comprising: filtering, by the processor, the diagnosis of the current health condition of the user to account for a known user health condition, prior to the modifying the graphical user interface to display the custom health report.

19. The computer program product of claim 15, further comprising: storing, by the processor, the diagnosis framework in a central repository, wherein the central repository is updated over time as additional tongue images are received from additional users.

20. The computer program product of claim 15, wherein the digital oral device is a toothbrush including at least one camera positioned on a head of the toothbrush, a display on a body of the toothbrush, and a wireless network interface for connecting to the computing system over a network.

* * * * *